(12) United States Patent
Borges et al.

(10) Patent No.: US 11,330,058 B2
(45) Date of Patent: *May 10, 2022

(54) REMOTE FLASHING DURING INFUSION

(71) Applicant: CareFusion 303, Inc., San Diego, CA (US)

(72) Inventors: Gregory Borges, San Diego, CA (US); Donald Halbert, San Diego, CA (US); Jeffrey L. Gaetano, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/875,783

(22) Filed: May 15, 2020

(65) Prior Publication Data

US 2020/0280608 A1 Sep. 3, 2020

Related U.S. Application Data

(63) Continuation of application No. 15/872,535, filed on Jan. 16, 2018, now Pat. No. 10,666,733, which is a
(Continued)

(51) Int. Cl.
*G06F 8/65* (2018.01)
*G16H 40/40* (2018.01)
(Continued)

(52) U.S. Cl.
CPC .......... *H04L 67/12* (2013.01); *A61B 5/0022* (2013.01); *A61B 5/02* (2013.01); *A61B 5/082* (2013.01);
(Continued)

(58) Field of Classification Search
CPC ......... H04L 67/12; H04L 67/10; H04L 67/34; G16H 20/17; G16H 40/40; G16H 10/00;
(Continued)

(56) References Cited

U.S. PATENT DOCUMENTS

| 6,363,282 B1 * | 3/2002 | Nichols | .................. G16H 40/67 |
|---|---|---|---|
| | | | 607/30 |
| 7,069,552 B2 | 6/2006 | Lindberg et al. | |

(Continued)

FOREIGN PATENT DOCUMENTS

JP 2013179973 A 9/2013

*Primary Examiner* — Daxin Wu
(74) *Attorney, Agent, or Firm* — Mintz, Levin, Cohn, Ferris, Glovsky and Popeo, P.C.

(57) ABSTRACT

A medical device controller operating in conjunction with a medical device determines one or more current versions of executable code associated with one or more processors in a medical device. Medical devices may include infusion pumps, other patient treatment devices as well as vital signs monitors. The medical device controller determines one or more current versions of executable code and configuration information associated with the one or more processors in the medical device. The medical device controller further determines which of the processors in the medical device require updated executable code, and which of the processors in the medical device require updated configuration information. The medical device controller distributes to the medical device as required at least one of the updated executable code and the updated configuration information. The medical device deploys the distributed updates, and activates the updates at a clinically appropriate time.

20 Claims, 6 Drawing Sheets

Related U.S. Application Data continuation of application No. 15/213,325, filed on Jul. 18, 2016, now Pat. No. 9,871,866, which is a continuation of application No. 14/153,998, filed on Jan. 13, 2014, now Pat. No. 9,424,020.

(51) Int. Cl.

| | | |
|---|---|---|
| H04L 67/12 | (2022.01) | |
| A61M 5/142 | (2006.01) | |
| H04W 4/50 | (2018.01) | |
| A61B 5/00 | (2006.01) | |
| H04L 67/00 | (2022.01) | |
| G16H 20/17 | (2018.01) | |
| A61B 5/02 | (2006.01) | |
| A61B 5/08 | (2006.01) | |
| A61B 5/145 | (2006.01) | |
| A61B 5/1455 | (2006.01) | |
| H04L 67/10 | (2022.01) | |
| G16H 10/00 | (2018.01) | |
| A61M 5/14 | (2006.01) | |

(52) U.S. Cl.
CPC .......... *A61B 5/145* (2013.01); *A61B 5/14552* (2013.01); *A61M 5/142* (2013.01); *A61M 5/14216* (2013.01); *A61M 5/14228* (2013.01); *G06F 8/65* (2013.01); *G16H 10/00* (2018.01); *G16H 20/17* (2018.01); *G16H 40/40* (2018.01); *H04L 67/10* (2013.01); *H04L 67/34* (2013.01); *H04W 4/50* (2018.02); *A61B 2560/045* (2013.01); *A61M 2005/1405* (2013.01); *A61M 2205/3561* (2013.01); *A61M 2205/3569* (2013.01); *A61M 2205/3584* (2013.01); *A61M 2205/3592* (2013.01); *A61M 2205/50* (2013.01); *A61M 2205/502* (2013.01); *A61M 2205/52* (2013.01); *A61M 2205/6054* (2013.01); *A61M 2205/6072* (2013.01)

(58) Field of Classification Search
CPC . H04W 4/50; A61B 5/02; A61B 5/082; A61B 5/145; A61B 5/14552; A61B 5/0022; A61B 2560/045; A61M 5/14216; A61M 5/14228; A61M 5/142; A61M 2205/52; A61M 2005/1405; A61M 2205/3561; A61M 2205/3569; A61M 2205/3584; A61M 2205/3592; A61M 2205/50; A61M 2205/502; A61M 2205/6054; A61M 2205/6072; G06F 8/65
See application file for complete search history.

(56) References Cited

U.S. PATENT DOCUMENTS

| | | | |
|---|---|---|---|
| 8,178,040 B2 * | 5/2012 | Brauer | A61M 1/16 422/44 |
| 8,387,112 B1 | 2/2013 | Ranjan et al. | |
| 8,843,203 B2 | 9/2014 | Lee et al. | |
| 9,135,393 B1 | 9/2015 | Blomquist | |
| 9,971,871 B2 | 5/2018 | Arrizza et al. | |
| 2003/0095648 A1 | 5/2003 | Kaib et al. | |
| 2004/0021693 A1 | 2/2004 | Monteleone | |
| 2004/0098715 A1 | 5/2004 | Aghera et al. | |
| 2005/0102669 A1 | 5/2005 | Marney et al. | |
| 2005/0108057 A1 | 5/2005 | Cohen et al. | |
| 2006/0080654 A1 | 4/2006 | Shelton | |
| 2006/0116639 A1 | 6/2006 | Russell | |
| 2007/0027506 A1 | 2/2007 | Stender et al. | |
| 2007/0098565 A1 | 5/2007 | Parsee et al. | |
| 2007/0253380 A1 | 11/2007 | Jollota et al. | |
| 2007/0258395 A1 | 11/2007 | Jollota et al. | |
| 2008/0004674 A1 | 1/2008 | King et al. | |
| 2008/0184219 A1 * | 7/2008 | Matsumoto | A61B 6/581 717/170 |
| 2008/0199894 A1 | 8/2008 | Galasso | |
| 2008/0243542 A1 | 10/2008 | Hammond et al. | |
| 2009/0063187 A1 * | 3/2009 | Johnson | G16H 40/20 705/2 |
| 2009/0157695 A1 * | 6/2009 | Roberts | G16H 40/67 |
| 2010/0037216 A1 * | 2/2010 | Carcerano | G06F 8/65 717/173 |
| 2010/0165795 A1 | 7/2010 | Elder et al. | |
| 2010/0165798 A1 | 7/2010 | Huang | |
| 2010/0245122 A1 | 9/2010 | Haralson et al. | |
| 2010/0313105 A1 * | 12/2010 | Nekoomaram | G06F 11/1433 714/807 |
| 2011/0178462 A1 | 7/2011 | Moberg et al. | |
| 2011/0213217 A1 * | 9/2011 | McKenna | A61B 5/14552 600/301 |
| 2011/0289497 A1 | 11/2011 | Kiaie et al. | |
| 2011/0307274 A1 | 12/2011 | Thompson et al. | |
| 2012/0036245 A1 | 2/2012 | Dare et al. | |
| 2012/0096451 A1 | 4/2012 | Tenbarge et al. | |
| 2012/0192170 A1 | 7/2012 | Kobayashi et al. | |
| 2013/0036412 A1 | 2/2013 | Birtwhistle et al. | |
| 2013/0036415 A1 | 2/2013 | Birtwhistle | |
| 2013/0046195 A1 | 2/2013 | McCabe et al. | |
| 2013/0067463 A1 | 3/2013 | Ito | |
| 2013/0169432 A1 | 7/2013 | Ozgul et al. | |
| 2013/0190834 A1 | 7/2013 | Ghosh et al. | |
| 2013/0275915 A1 | 10/2013 | Wang | |
| 2013/0289657 A1 | 10/2013 | Rodriguez | |
| 2013/0297330 A1 | 11/2013 | Kamen et al. | |
| 2013/0317753 A1 | 11/2013 | Kamen et al. | |
| 2013/0317837 A1 | 11/2013 | Ballantyne et al. | |
| 2013/0346108 A1 * | 12/2013 | Kamen | G16H 40/63 705/3 |
| 2014/0019952 A1 | 1/2014 | Shamsaasef et al. | |
| 2014/0031884 A1 | 1/2014 | Elghazzawi | |
| 2014/0033002 A1 | 1/2014 | Nekoomaram et al. | |
| 2014/0163425 A1 | 6/2014 | Tran | |
| 2014/0276426 A1 | 9/2014 | Borges et al. | |
| 2015/0025498 A1 | 1/2015 | Estes | |

* cited by examiner

REMOTE FLASHING DURING INFUSION

CROSS REFERENCE TO RELATED APPLICATION

This application is a continuation of U.S. patent application Ser. No. 15/872,535 filed on Jan. 16, 2018, entitled "REMOTE FLASHING DURING INFUSION," issuing on May 26, 2020 as U.S. Pat. No. 10,666,733, and is a continuation of U.S. patent application Ser. No. 15/213,325 filed Jul. 18, 2016, now U.S. Pat. No. 9,871,866, entitled "REMOTE FLASHING DURING INFUSION," which is a continuation of U.S. patent application Ser. No. 14/153,998 filed Jan. 13, 2014, now U.S. Pat. No. 9,424,020 entitled "REMOTE FLASHING DURING INFUSION," the disclosure of which is hereby incorporated by reference in its entirety.

TECHNICAL FIELD

The subject matter described herein relates to a medical device system. In particular, the current subject matter is directed to a system for coordinated operation of multiple medical devices such as infusion pumps and vital signs monitors including the coordination of program and configuration updates for one or more processors contained in medical devices.

BACKGROUND

Medical device systems may utilize a plurality of different medical devices that are distinct stand-alone or independent medical devices. For example, some conventional infusion pumping systems may include up to about four functionally distinct stand-alone infusion pumps. Conventional infusion pumps are typically stand-alone complex devices that are only able to provide independent complex infusion functions. As such, coordination or control of the devices collectively is complex and difficult. Moreover, purchasing of the complex stand-alone devices can be financially burdensome.

Hospitals using each of several different models of pumps, each employing distinct user interfaces, makes both learning and practicing their operation more time consuming with risk of error elevated. For instance, there may be pumps for syringe, large volume, patient controlled analgesia, anesthesia and other uses. These difficulties can be compounded when there are other medical devices being used for patient care including various types of vital sign monitors and the like.

Furthermore, many medical devices contain one or more programmable processors and memory with executable code and configuration information that must be updated from time to time. Coordination of updates across different medical devices and across multiple medical devices is important to reduce the potential for errors in patient treatment and the tracking of patient treatment.

SUMMARY

In one aspect, a medical device controller operating in conjunction with a medical device determines one or more current versions of executable code and configuration information associated with one or more processors in a medical device. The medical device controller determines one or more current versions of executable code and configuration information associated with the one or more processors in the medical device. The medical device controller further determines which of the one or more processors in the medical device require updated executable code, and which of the one or more processors in the medical device require updated configuration information. The medical device controller distributes to the medical device as required at least one of the updated executable code and the updated configuration information. The medical device deploys the distributed updates and activates the updates at a clinically appropriate time.

In a related aspect the executable code can include at least one of an operating system and an application, and the configuration information can include values which affect the functioning of the medical device that are modifiable by a user.

In a related aspect, at least one communications interface wirelessly couples the medical device controller to the medical device. The at least one communications interface can include an optical data transceiver such as an infrared optical data transceiver. In some variations, there are a plurality of optical data transceivers and the at least one communications interface includes a communications bus coupled to each optical data transceiver. The at least one communications interface can wirelessly and communicatively couple the medical device controller to at least one medical device module.

A medical device module may couple into a modular medical device system that may provide for inductive powering of the medical device module. Medical devices may also be stand-alone and are not coupled into a modular system.

The at least one communications interface can be operable to receive and transmit data from at least one remote computing system via a wired and/or wireless communication link. The at least one communications interface can be operable to receive and transmit data from at least one medical device (i.e., a medical device that is not a medical device module) via a wired or wireless connection.

In another aspect, a medical device (or medical device module) receives at least one update including one or more of updated executable code and updated configuration information from a medical device controller for one or more processors in the medical device. The medical device further deploys the received at least one update by determining the appropriate processor in the medical device associated with the at least one update and transferring the at least one update to an appropriate storage associated with the appropriate processor. The medical device further activates at a clinically appropriate time the deployed update by selecting to use the at least one update at the appropriate processor during operation of the medical device.

A wide variety of medical devices and medical device modules can be used in conjunction with the medical device controller. For example, the system can be used with infusion pumps such as syringe pumps, patient controlled infusion pumps (e.g., patient-controlled analgesia (PCA) system), large volume infusion pumps, peristaltic pumps, and the like. The medical device modules can also be one or more of a vital signs monitor, cardiac output monitors, gastric tonometers, an SpO2 sensor, an EtCO2 sensor, a blood analyte monitor, an identification module, a barcode scanner, and a radio frequency identification (RFID) scanner.

In another interrelated aspect, an infusion pump includes at least one data processor, memory storing instructions for execution by the at least one data processor, and at least one pumping sub-system for pumping fluid passing therethrough (via a tubing set, an IV cassette, etc.). Such an infusion pump can be configured such that it does not include an external electrical galvanic connector. In some variations, the infusion pump includes an inductive receiver for being inductively powered by an inductive backplane of a modular medical device system.

In a further interrelated aspect, a medical device includes at least one data processor, memory storing instructions for execution by the at least one data processor, and a housing. The housing may have a shape and size to be secured by an inductive backplane of a modular medical device system. A medical device module may also include an inductive receiver for powering medical device module. An inductive backplane may inductively power the inductive receiver when the housing of the medical device module is secured thereto.

Computer program products are also described that comprise non-transitory computer readable media storing instructions, which when executed one or more data processors of one or more computing systems, causes at least one data processor to perform operations herein. Similarly, computer systems are also described that may include one or more data processors and a memory coupled to the one or more data processors. The memory may temporarily or permanently store instructions that cause at least one processor to perform one or more of the operations described herein. In addition, methods can be implemented by one or more data processors either within a single computing system or distributed among two or more computing systems. Such computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection (wired or peer-to-peer wireless) between one or more of the computing systems, etc.

The subject matter described herein provides many advantages. For example, the current subject matter provides enhanced usability for clinicians both with regard to the ease of coupling and decoupling medical device modules from the system and in connection with the various user interfaces provided by the system. Further advantages include the coordinated distribution to medical devices of updates to executable code and configuration information, the deployment of the updates within the medical devices, and the activation of the deployed updates. Coordinating executable code updates and configuration information updates assures compatibility of the configuration data and the executable code stored in the medical device. Moreover, when the processors in the medical device or system are updated together, operational compatibility between the processors can be assured. Furthermore when all the medical devices in the system are updated together, compatibility between the medical devices in the system can also be assured. By coordinating the configuration information updates and executable code updates, the number of combinations of executable code versions and configuration information versions that must be tested to assure compatibility is reduced resulting in a more robust and reliable system. Also, by not re-sending updates of executable code or configuration information that medical devices have already received, time and bandwidth resources are conserved by eliminating unneeded or duplicate updates.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

Like reference symbols in the various drawings indicate like elements.

DETAILED DESCRIPTION

Figure 1:
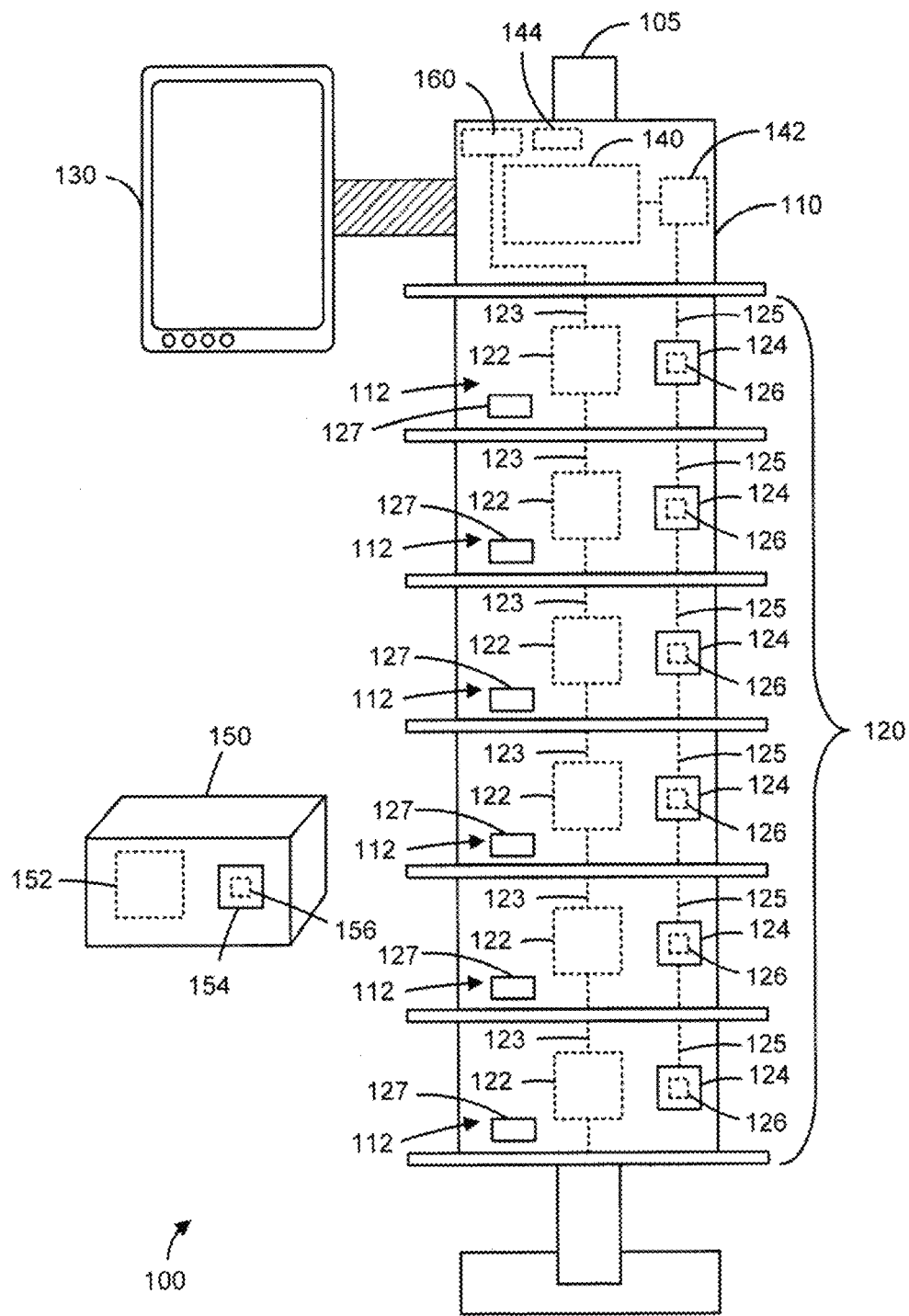
FIG. 1 is a diagram illustrating a modular medical device system.

FIG. 1 is a diagram 100 illustrating a modular medical device system 110. The system 110 comprises a backplane 120 that can be mounted on a pole 105. The backplane 120 can mechanically couple to and secure one or more medical device modules 150 (also referred to herein as a medical device) along each of a series of pre-defined mounting seats 112. In some variations, each of the mounting seats 112 are uniform in size and spacing, while in other variations different sizing and/or spacing can be used to accommodate medical device modules 150 having different exterior dimensions. In addition, the mounting seats 112 can be arranged along a single axis (e.g., a vertical axis as illustrated, etc.) or they can be arranged along two or more axes. The mounting seats 112 can each have one or more mechanical elements to detachably affix the medical device modules 150 to the backplane 120.

In addition to allowing the medical device modules to be affixed to the system, the backplane 120 can provide non-contact inductive power to one or more medical device modules 150. The backplane 120 can, for each mounting location, comprise an inductive transmitter 122 for non-contact powering of a medical device module 150. A corresponding inductive receiver 152 on the medical device module 150 can, when the medical device module 150 is affixed to the mounting seat 112, be inductively coupled with inductive transmitter 122 of backplane 120. In general, energy is sent via an inductive (magnetic) coupling between inductive transmitter 122 and inductive receiver 152. As a result, there is a wireless (no galvanic contact) energy transfer between inductive backplane 120 and medical device module 150. Moreover, an electrical galvanic connector, as is typical for powering conventional medical devices, is not required to provide power to medical device module 150. Use of non-contacting energy transfer avoids metallic contacts between medical device module 150 and a power source which may be damaged, require special cleaning and pose risk of electrical heating, smoke or fire. Each inductive transmitter 122 can be coupled to an induction bus 123 which in turn is connected to a power source 160 (e.g., a wired connection to an outlet, a battery, etc.) to enable the inductive coupling of each inductive transmitter 122.

The backplane 120 can also provide an optical communications interface to one or more medical device modules 150 via respective optical communications ports 124 and optical transceivers 126 corresponding to each mounting seat 112. The medical device modules 150 can have corresponding optical communications ports 154 and optical transceiver 156 which can be optically aligned with the optical communication port 124 on the backplane 120 when the medical device module 150 is affixed to the backplane 120 so that a bi-directional data feed can be established between the optical transceivers 126, 156. Such data can relate to a variety of aspects including, but not limited to, data characterizing operation of the medical device module 150, data for controlling (e.g., modifying, monitoring, etc.) one more attributes of the medical device module 150 (e.g., updates to executable program code, configuration updates, asset locations, status information, historical data, patient information, patient treatment parameters, medication administration information, etc.), and the like. Executable program code that may be stored in memory and runs on a processor is sometimes referred to as software. The data exchanged via the optical transceivers 126, 156 can comprise any data generated or otherwise used by a medical device module 150 or a caregiver using same. The data transmitted to the backplane 120 can be consumed locally by the system 110 and/or it can be transmitted to one or more remote systems/devices coupled to the system 110 via a wired or wireless communications link. The optical data transceivers 126, 156 can be infrared (IR) data transceivers such that optical data 146 is propagated by IR light as the transmission medium. The optical data transceivers can be coupled to a communications bus 125 that in turn is coupled to a communications interface 142. The communications interface 142 can, in turn, be coupled to the control unit 140. In addition or in the alternative, a second communications interface 144 can provide an outward interface for the modular medical device system 110 that provides a wired or wireless connection to other devices and/or networks. It will be appreciated that any number of communications interfaces can be used, including one communications interface for each optical data transceiver 126/seat 112.

The control unit 140 can be hardware, software, or a combination of both. For example, the control unit 140 can be a specially designed hardware module including at least one processor and memory with specialized software (e.g. executable code) used to control any aspect of a medical device module 150 coupled to the system 110. In other cases, the control unit 140 can be a software module (or series of modules) used to control any aspect of a medical device module 150 coupled to the system 110. As used herein, unless otherwise specified, the term control shall relate to any type of data exchange with a medical device module 150 by the control unit 140 including data generated by a medical device module 150 and data used by a medical device module 150 (software updates, power state changes, etc.). For example, the control unit 140 can be used to selectively wake up medical device modules 150 coupled to the inductive backplane 120 from a sleep state. Furthermore, the control unit 140 can be coupled to one or more remote computing systems (via the communications interface 144) to allow for the remote control of the medical device modules 150.

Each mounting seat 112 can include a shelf with dove tail features extending from a housing of the system 110. Each medical device module 150 can include a latch mechanism on a top rear edge that affixes to the housing of the system 110. The latch mechanism can reduce load on the shelf and can cause the medical device module 150 to rotate back into contact with the system 110 under load (rather than deflect away from it). This arrangement can help insure that the inductive transmitter 122 is positioned properly and secured in relation to the inductive receiver 152.

Each mounting seat 112 can include a proximity sensor 127 that can detect the presence of a medical device module 150. The proximity sensors 127 can be optical, electric, electro-mechanical, and/or mechanical devices. For example, the proximity sensors 127 can comprise a Hall effect sensor and/or a mechanical switch. The presence of a medical device module 150 can be used to initiate, for example, inductive powering by the corresponding inductive transmitter 122 and/or communications via the communications interface 142. The proximity sensor 127 can also indicate an alarm condition when a medical device module 150 is not completely secured so that appropriate actions can be taken.

Medical device module 150 can be any medical device that is compatible for scalability in a modular medical device system. For instance, the modular medical device system 110 can utilize one or more medical device modules 150 depending on the functionality that is needed for proper care of a patient. Moreover, a modular medical device system 110 can be scaled up to incorporate additional medical device modules 150 and also scaled down by removing medical device modules 150.

For example, if patient care requires only one infusion pump, then the modular medical device system 110 can include a single affixed infusion pump. Moreover, if patient care requires two infusion pumps, then the modular medical device system 110 can be scaled up to include an affixed additional infusion pump.

Medical device module 150 can include, but is not limited to, an infusion pump (e.g., a large volume pump (LVP), a syringe pump), a patient-controlled analgesia (PCA) system, a vital signs monitor (VSM) (e.g., an SpO2 sensor, an EtCO2 sensors, cardiac output monitors, gastric tonometers, etc.), a bedside blood analyte analyzer (e.g. blood glucose), an Auto-ID module (barcode scanner and RFID), and other devices which measure physiological parameters associated with a patient and/or assist with the clinical care of the patient (and such medical device modules 150 may not necessarily measure physiological parameters of the patient).

Modular medical device system 110 can also comprise a display unit 130 that provides a unified interface that characterizes the operation of various medical device modules 150 coupled to the backplane 120. The display unit 130 can comprise a touch screen interface that allows a user to selectively view and alter performance parameters/metrics of individual medical device modules 150, concurrently view performance parameters/metrics of multiple medical device modules 150, and additionally orchestrate complex sequences of infusions/operations from multiple medical device modules 150. The display unit 130 can be affixed to an outer housing of the modular medical device system 130/inductive backplane 120 by a tilt and swivel arm mount that allows the display unit to be moved on different sides of the system 110 and/or to change varying positions (to accommodate different positions/heights of caregivers).

The display unit 130 can include a speaker to provide audio cues relating to various aspects of medical device modules 150 (in other versions the speaker is located elsewhere in the system 110). When the medical device modules 150 are coupled to the backplane 120, audio cues such as alarms for such medical device modules 150 can be delegated so that the system 110 handles the alarms whether via an audio and/or visual cue in the display unit 130 or by an audio cue generated elsewhere in the system 110. In some cases, some alarms can be still be handled by a medical device module 150 while other alarms are handled by the system 110.

Figure 2:
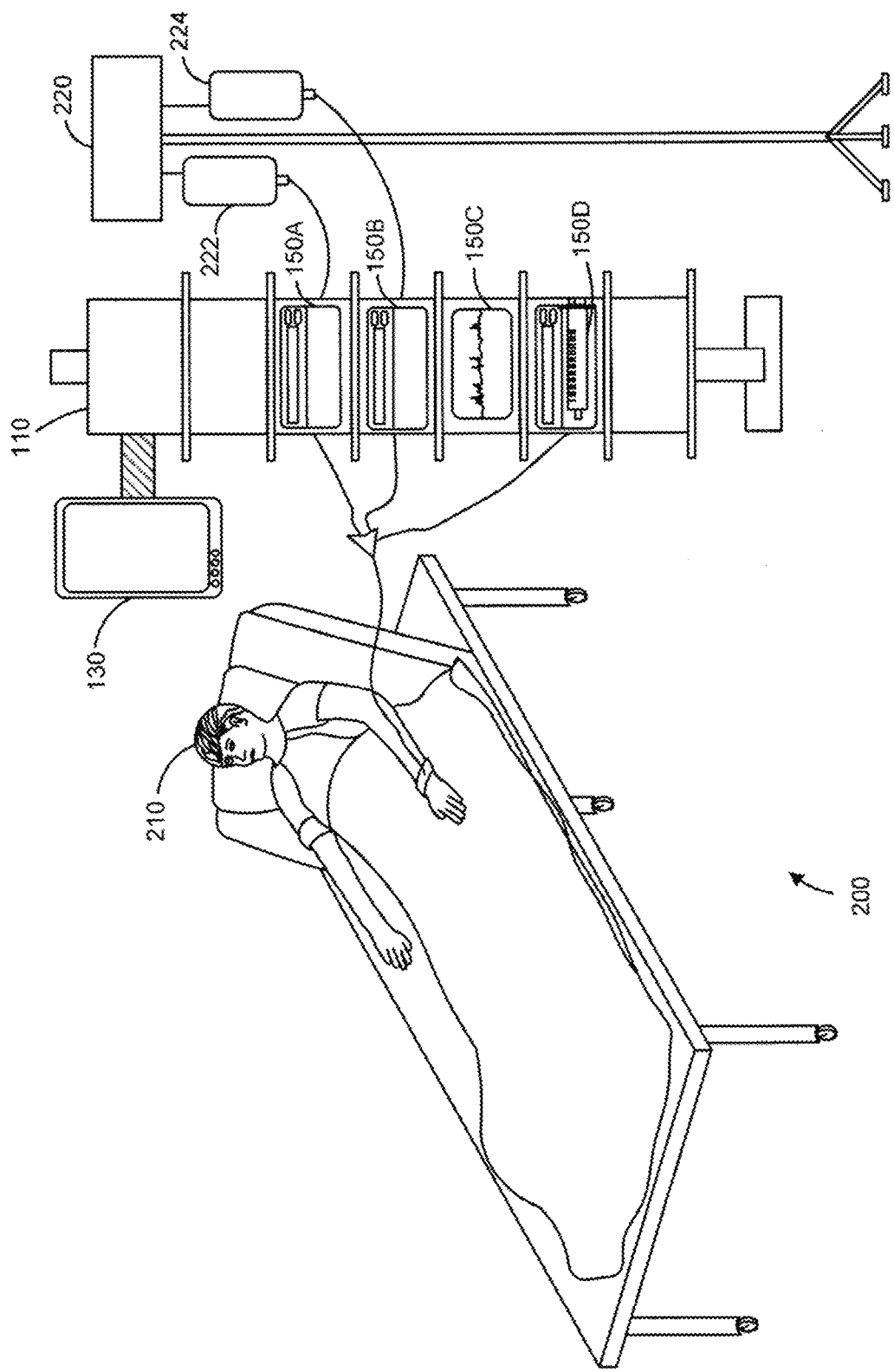
FIG. 2 is a diagram illustrating a modular medical device system in a clinical setting.

FIG. 2 is a diagram 200 illustrating a modular medical device system 110 in a clinical setting. In particular, in this view, the modular medical device system 110 is coupled to two infusion pumps 150A, 150B, a vital signs monitor 150C, and a syringe pump 150D. The infusion pumps 150A and 150B are respectively fluidically coupled to two fluid/medication containers 222, 224 suspended from an IV pole 220. In addition, each of the infusion pumps 150A and 150B and the syringe pump 150D are fluidically coupled to an IV catheter inserted into a patient 210 so that the corresponding fluids can be delivered to the patient. The modular medical device system 110 monitors and/or controls how fluids from the respective sources 150A, 150B, 150D are delivered to the patient 210. It will be appreciated that varying numbers of medical device modules 150 can be utilized depending on the particular condition of and/or treatment the patient 210.

Figure 3:
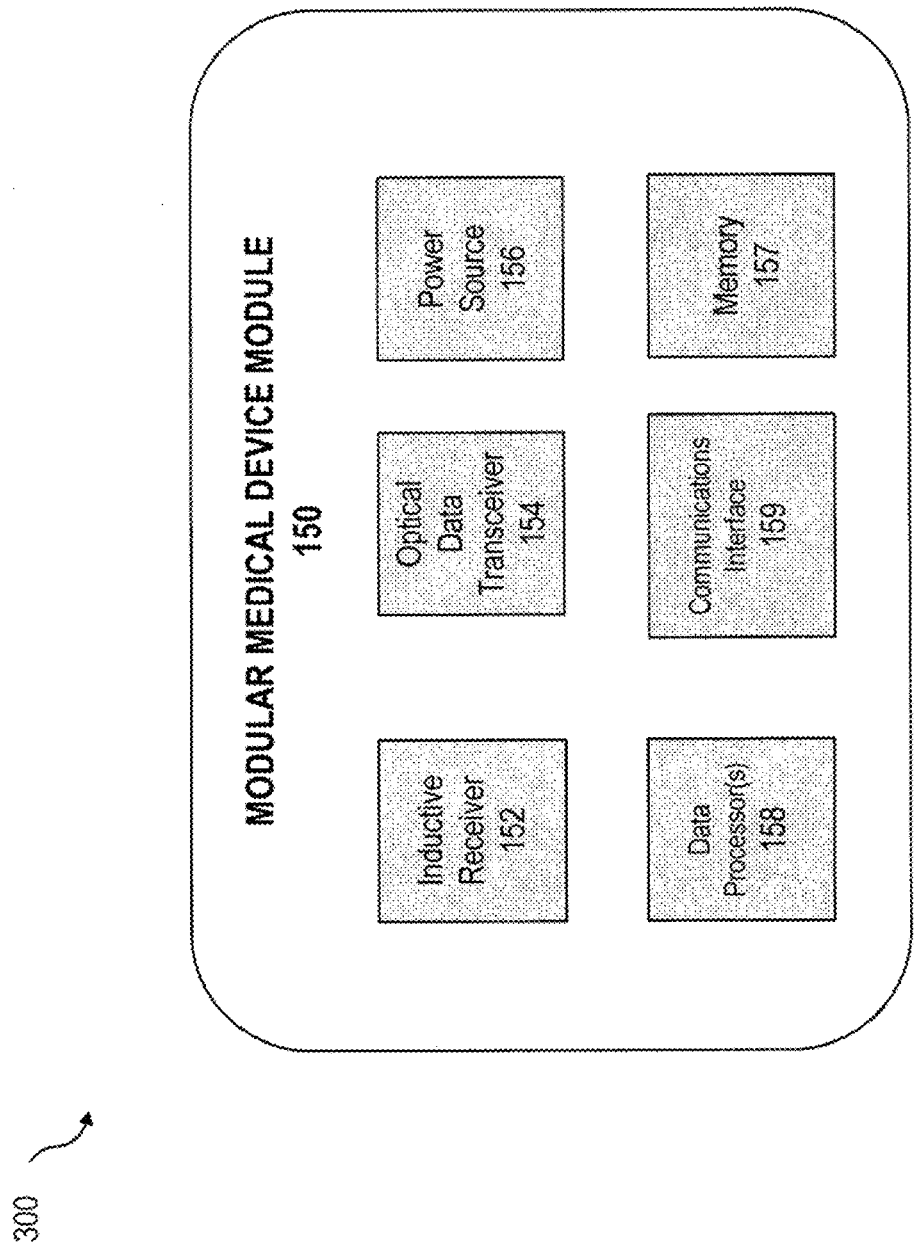
FIG. 3 is a logic diagram illustrating a medical device module.

FIG. 3 is a logic diagram 300 of a medical device module 150. Each medical device module 150 can include a secondary power source 156 such as a battery or a wired connection to an external power source. For example, the secondary power source 156 can power medical device module 120 when inductive receiver 152 is unable to power medical device module 150. In one scenario, medical device module 150 is an infusion pump that is associated with (and fluidly communicating with) a patient. If the patient is moved to another location (e.g., to an x-ray room which is away from inductive backplane 110), then medical device module 150 must also move with the patient away from inductive backplane 120 in order to continue the current infusion without interruption. At a certain distance from inductive backplane 120, inductive receiver 152 cannot be energized by inductive backplane 120 and therefore cannot power medical device module 150. In other cases, the inductive backplane 120 may be turned off or operating in a mode not allowing the inductive receiver 152 to be energized. Accordingly, power source 156 (which may also be charged through inductive receiver 152) is able to provide the requisite power for medical device module 150. In one variation, the power source 156 is a battery that can keep medical device module 150 operational in a range of about two to ten hours. It is noted that when a medical device module 150 is reattached to the prior inductive backplane or a different inductive backplane, information required to continue the infusion stored in memory 157, without interruption, can be transmitted from the medical device module 150 to the backplane (and to the control unit 140).

Each medical device module 150 can also include memory 157 and at least one data processor 158. The memory 157 can store executable code for execution by the at least one data processor 158 for use, for example, in the operation of the medical device module in a clinical setting. The memory 157 can also store data relating to the operation of the medical device module such as data characterizing how the medical device module 150 is used and parameters relating to same (e.g., number of hours operated, thresholds for alerts, etc.), performance and status information, and well as other aspects relating to the use of such medical device module 150 such as patient data, medication administration data, patient treatment parameters, etc. Some or all of the data relating to the operation of the medical device module may be configuration information.

As used herein, configuration information is any information that is modifiable by a system user such as information modifiable by the customer, hospital, administrator, nurse, physician, pharmacy, network administrator, and so on. Configuration information can include clinical data sets, international language texts, and syringe lists. Clinical data sets may include patient treatment information and other information. International language texts can include text used in the menus and settings of the user display such as display unit 130 or a display incorporated into medical device 150. Syringe lists include compatible syringes with a medical device such as an infusion pump 150A, 150B, or syringe pump 150D. Different medical devices may have different configuration information.

Each medical device module 150 can also comprise an additional communications interface 159 other than the optical data transceiver 154 (in some variations the optical data transceiver 154 may not form part of the medical device module 150 and so the communications interface 159 may be the only gateway for communication outside of the medical device module 150). This communications interface 159 can be fixed and/or wireless and be used to communicate to computer networks and peer-to-peer pairing with other devices when the medical device module 150 is not coupled to the backplane 120.

In some implementations, the communications interface 159 can be used in addition or instead of the optical data transceiver 154 when the medical device module 150 is coupled to the backplane 120. For example, the medical device module 150 can be seated on the backplane 120 but not have an optical data transceiver. In such a scenario, the communications interface 159 can wirelessly communicate with the control unit 140 of the modular medical device system 110 so that the operation of the medical device module 150 can be monitored and/or controlled by the modular medical device system 110 (whether or not the medical device module 150 is seated). Various types of wireless communications can be used (for this and other aspects described herein) such as short distance protocols such as BLUETOOTH, near field communication (NFC), WiFi, ZIGBEE, and the like.

As noted above, the system 110 comprises a control unit 140 (which in turn can comprise at least one data processor and memory for storing instructions for execution by the at least one data processor and/or data characterizing or otherwise relating to the operation of medication device modules 150). The control unit 140 can act to individually monitor and/or control the operation of the medical device modules 150 affixed to the backplane 120 such that the functionality of the medical device modules 150, alone and/or in combination are increased. In some cases, the control unit 140 can orchestrate the operation of multiple medical device modules 150. For example, certain sequences of operation and/or concurrent operation can be defined amongst the medical device modules 150. Such an arrangement can permit, for example, coordinated infusion from different fluid sources. Some medical device modules 150 can have the ability to function fully independent of the control unit 140 for the purpose of basic operations. However, the modules acquire more complex abilities and functionality when operating under the command and coordination of the controller.

In some clinical settings, backplanes 120 can be utilized to serve a single patient. With such an arrangement, each inductive backplane 120 can have local communication with the other inductive backplanes 120 serving the same patient to provide coordination of functionality and data. The communication can be wired and/or wireless using, for example, short range digital radio technology, WiFi, optical data transceivers, BLUETOOTH, ZIGBEE, NFC, and the like.

In some implementations of the modular medical device system 110 of FIG. 1, communications with medical device modules 150 utilize a communications protocol different from the optical sub-systems (124, 125, 126, 142). For example, in some variations, the inductive transmitters 122 and inductive bus 123 can be used to exchange data with the inductive receiver 152 to affect a near-field magnetic induction communication system. Such an arrangement can provide a short range wireless physical layer that communicates by coupling a tight, low-power, non-propagating magnetic field between the inductive transmitter 122 and the inductive receiver 152. The transmitter coil in the inductive transmitter 122 can modulate a magnetic field which is measured by the inductive receiver 152 in another device. It will be appreciated that the communications are bi-directional and as such, the inductive receiver 152 can also transmit data to the inductive transmitter 122.

In other variations, the modular medical device systems 110 can communicate and exchange data with the medical device modules 150 via a wireless communications protocol including, but not limited to short range digital radio technology, WiFi, optical data transceivers, BLUETOOTH, ZIGBEE, NFC, and the like.

Figure 4:
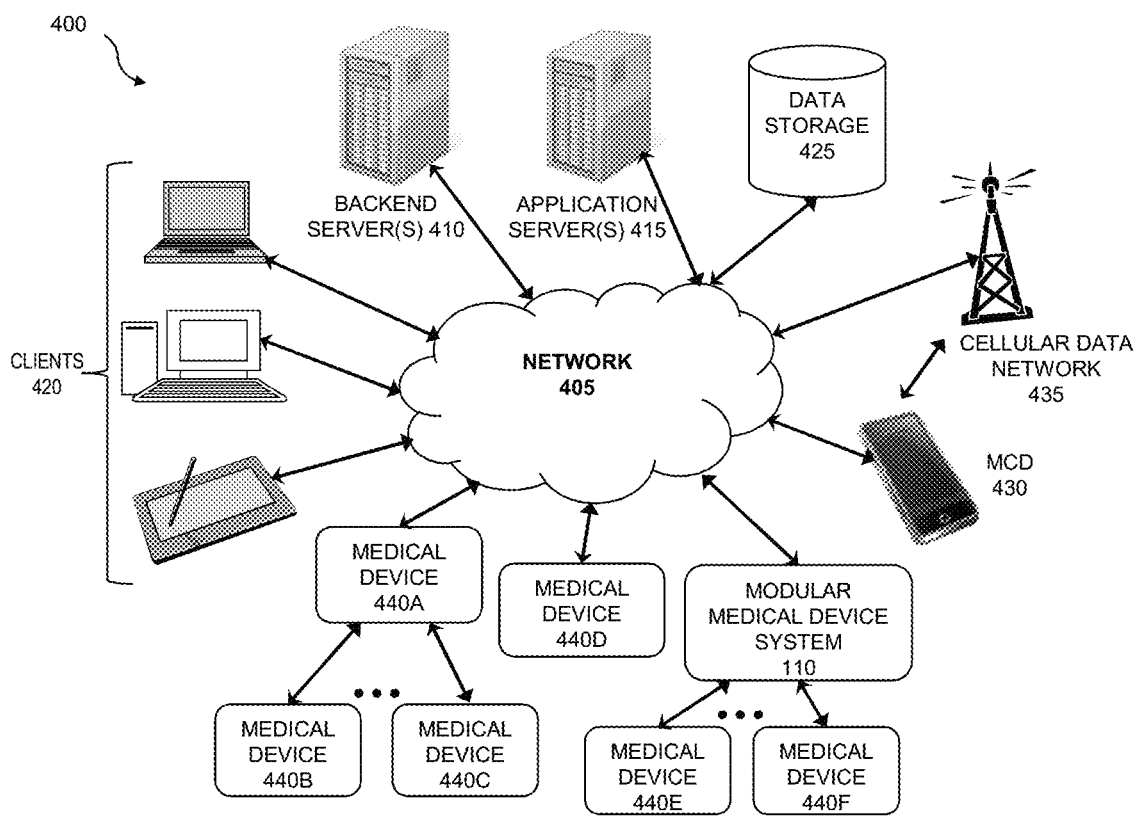
FIG. 4 is a diagram illustrating a computing landscape including a modular medical device system.

FIG. 4 is a system diagram illustrating a computing landscape 400 within a healthcare environment such as a hospital that includes modular medical device system as well as stand-alone medical devices. Various devices and systems, both local to the healthcare environment and remote from the healthcare environment, can interact via at least one computing network. This computing network can provide any form or medium of digital communication connectivity (i.e., wired or wireless) amongst the various devices and systems. Examples of communication networks include a local area network ("LAN"), a wide area network ("WAN"), and the Internet. In some cases, one or more of the various devices and systems can interact directly via peer-to-peer coupling (either via a hardwired connection or via a wireless protocol such as Bluetooth or WiFi). In addition, in some variations, one or more of the devices and systems communicate via a cellular data network.

The modular medical device systems 110 can include at least one communications interface that can access the computing network 405 either via a fixed wired connection or via a wireless connection (via, for example, one or more access points). In addition, the modular medical device system 110 can also couple to other components within the computing landscape 400 via direct wired or wireless peer-to-peer coupling. Furthermore, in some cases, one or more of the medical devices 440A-D can be self-contained and are not connected to modular medical device system 110. Modular medical device 150 and medical device 440 can perform the same or similar functions for providing patient treatment. The modular medical device system 110 can transmit data via the computing network 405 to any of the other components within the landscape 400. In addition, the modular medical device system 110 can receive data from the computing network 405 relating to monitoring and in some cases controlling one or more attributes of the medical device modules 150 or medical devices 440 (e.g., software updates, configuration updates, historical data, status information, assets location, patient information, etc.).

In particular, aspects of the computing landscape 400 can be implemented in a computing system that includes a back-end component (e.g., as a data server 410), or that includes a middleware component (e.g., an application server 415), or that includes a front-end component (e.g., a client computer 420 having a graphical user interface or a Web browser through which a user may interact with an implementation of the subject matter described herein), or any combination of such back-end, middleware, or front-end components. Client 420 and servers 410, 415 are generally remote from each other and typically interact through the communications network 405. The relationship of the clients 420 and servers 410, 415 arises by virtue of computer programs running on the respective computers and having a client-server relationship to each other. Clients 420 can be any of a variety of computing platforms that include local applications for providing various functionality within the healthcare environment. Example clients 420 include, but are not limited to, desktop computers, laptop computers, tablets, and other computers with touch-screen interfaces. The local applications can be self-contained in that they do not require network connectivity and/or they can interact with one or more of the servers 410, 415 (e.g., a web browser).

A variety of applications can be executed on the various devices and systems within the computing landscape 400 such as electronic health record applications, medical device monitoring, operation, and maintenance applications, scheduling applications, billing applications and the like. As another example, the applications can comprise a collection of enterprise-based applications that provide dose error reduction software (DERS) for the computing landscape 400 that incorporates a role-based view of infusion data, provides a comprehensive platform for connectivity to external hospital applications, and enables directed maintenance and calibration activities for devices, storage of clinical and device history, etc. As a further example, the applications can provide for remote alarms management and/or asset tracking for medical device modules 150 coupled to one or more of the modular medical device system 110, and for medical devices 440.

The network 405 can be coupled to one or more data storage systems 425. The data storage systems 425 can include databases providing physical data storage within the healthcare environment or within a dedicated facility. In addition, or in the alternative, the data storage systems 425 can include cloud-based systems providing remote storage of data in, for example, a multi-tenant computing environment. The data storage systems 425 can also comprise non-transitory computer readable media.

Mobile communications devices (MCDs) 430 can also form part of the computing landscape 400. The MCDs 430 can communicate directly via the network 405 and/or they can communicate with the network 405 via an intermediate network such as a cellular data network 435. Various types of communication protocols can be used by the MCDs 430 including, for example, messaging protocols such as SMS and MMS. In some cases, the MCDs 430 can receive alerts generated from the operation of the medical device modules 150 coupled to the backplane 120 and/or they can otherwise be used to monitor the operation of such medical device modules 150.

Various types of medical devices 440 can be used as part of the computing landscape 400. These medical devices 440 can comprise, unless otherwise specified, any type of device or system with a communications interface that characterizes one or more physiological measurements of a patient and/or that characterize or are used for the treatment of a patient. In some cases, the medical devices 440 communicate via peer to peer wired or wireless communications with another medical device 440 (as opposed to communicating with the network 405). For example, the medical device 440 can comprise a bedside vital signs monitor that is connected to other medical devices 440 (and/or the modular medical device system 110), namely a wireless pulse oximeter and to a wired blood pressure monitor. One or more attributes of the medical devices 440 can be locally controlled by a clinician, controlled via a clinician via the network 405, and/or they can be controlled by one or more of a server 410, 415, a client 420, a MCD 430, and/or another medical device 440, or the modular medical device system 110.

The computing landscape 400 can provide various types of functionality as may be required within a healthcare environment such as a hospital. For example, a pharmacy can initiate a prescription via one of the client computers 420. This prescription can be stored in the data storage 425 and/or pushed out to other clients 420, an MCD 430, and/or one or more of the medical devices 440/medical device modules 150. In addition, the medical devices 440,150 can provide data characterizing one or more physiological measurements of a patient and/or treatment of a patient (e.g., medical device 440 can be an infusion management system, etc.). The data generated by the modular medical device system 110 and the medical devices 440 can be communicated to other medical devices 440, the servers 410, 415, the clients 420, the MCDs 430, and/or stored in the data storage systems 425.

Medical devices 440A-F, 150 can contain one or more processors and at least one memory. Executable program code (e.g. software or executable code) is stored in the at least one memory where the executable program code causes the medical devices 440A-F, 150 to perform operations required for patient care. Configuration information can also be stored in the at least one memory. Configuration information is any information that is modifiable by a system user such as information modifiable by the customer, hospital, administrator, nurse, physician, pharmacy, network administrator, and so on. In order to provide patient care, the medical device 440A-F, 150 may require a current version of software stored in the at least one memory and may also require a current version of configuration information. A medical device 440A-F, 150 may contain multiple processors. Each processor may require current software and configuration information. From time to time, the software and/or configuration information of the medical device 440A-F, 150 may need to be updated. In some implementations, updates to executable program code and configuration information are distributed to medical devices 440, 150 while the medical devices are providing patient treatment or otherwise operating. At a clinically appropriate time, the updates can be deployed within the medical devices 440, 150 and activated for use by the medical devices 440, 150. Activation can be performed so that it does not interfere with patient treatment.

Figure 5:
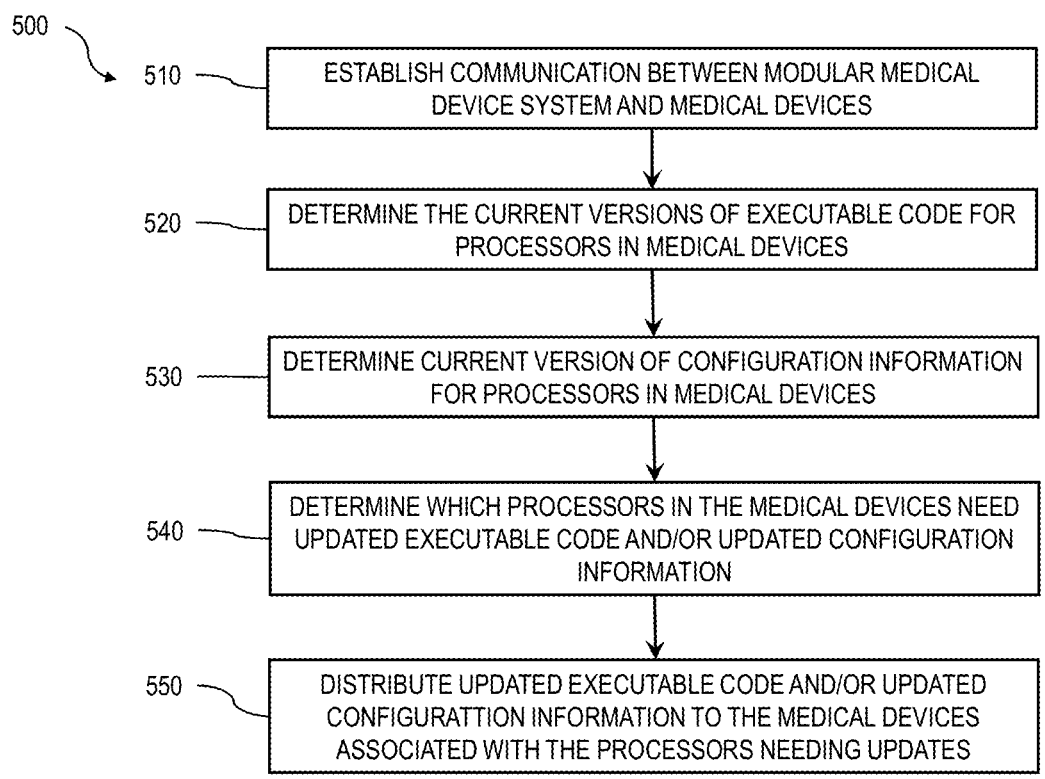
FIG. 5 is an example of a process 500 performed at a modular medical device system to provide updated executable code and/or updated configuration information to the processors in a medical device.

FIG. 5 is an example of a process 500 performed at a medical device system/modular medical device system to update the executable code and/or configuration information in a medical device/medical device module. At 510, communication is established between the medical device(s) and the modular medical device system. At 520, the modular medical device system determines the current version(s) of the executable code stored at the medical device(s) for the processor(s) in the medical device(s). At 530, the modular medical device system determines the version(s) of the configuration information stored at the medical device(s) for the processor(s) in the medical device(s). At 540, the modular medical device system determines which medical device(s) requires updated executable code and which medical device(s) requires updated configuration information. At 550, the modular medical device system distributes updated executable code and/or configuration information for the processor(s) in the medical device(s) to the medical device(s) via a communication path.

At 510, communication is established between the medical device(s) 440, 150 and the modular medical device system 110 (or servers 410, 415, or client 420). In some implementations, communication is established via a wired or wireless network, or via backplane 120, optical communications ports 124, optical transceivers 126,156, and/or communications interface 159, 142. In some implementations, communication may be established while one or more of the medical devices 440, 150 are operating. For example, a medical device such as infusion pump 150A may be providing an infusion to a patient while communication is established with the modular medical device system 110.

At 520, the modular medical device system 110 (or servers 410, 415, or client 420) determines the current version(s) of the executable code stored at the medical device(s) 440, 150 for the processor(s) in the medical device(s) 440, 150. For example, modular medical device system 110 may establish communication at 510 with medical device 440E and 440F. In this example, medical device 440E has one processor and medical device 440F has five processors. Modular medical device system 110 determines the version of the executable code for the one processor in medical device 440E, and the versions of the executable code for each of the five processors in medical device 440F. The determination of the version(s) of the executable code at the processor(s) may be performed via a message exchange between the medical device 440E, 440F and the modular medical device system 110 over the established communication 510.

At 530, the modular medical device system 110 (or servers 410, 415, or client 420) determines the version(s) of the configuration information stored at the medical device(s) 440, 150 for the processor(s) in the medical device(s) 440, 150. For example, modular medical device system 110 may establish communication at 510 with medical device 440E and 440F. In this example, medical device 440E has one processor and medical device 440F has five processors. Modular medical device system 110 then determines the version of any configuration information associated with the one processor in medical device 440E and for each of the five processors in medical device 440F. The determination of the version(s) of the configuration information at the processor(s) may be performed via a message exchange between the medical device 440E, 440F and the modular medical device system 110 over the established communication 510.

At 540, the modular medical device system 110 determines which medical device(s) 440, 150 requires updated executable code and which medical device(s) 440, 150 requires updated configuration information. In some implementations, modular medical device system 110 has a table or list of current (updated) versions of the executable code for the processor(s) in the medical device(s) 440, 150. Modular medical device system 110 may have a table or list of current versions (updated) of the configuration information for the processor(s) in the medical device(s) 440, 150. The determination of which medical devices 440, 150 require updating may be performed by comparing the version(s) of executable code stored at the medical devices 440, 150 with the table of current version(s) of executable code in the executable code table and comparing the version(s) of configuration information stored at the medical devices 440, 150 with the current version(s) of configuration information in the configuration table.

At 550, the modular medical device system 110 (or servers 410, 415, or client 420) distributes to the medical device(s) 440, 150 via the established communication path 510 any updated executable code required by the processor(s) in the medical device(s) 440, 150. The modular medical device system 110 also distributes via the established communication path 510 any updated configuration information required by the processor(s) in the medical device(s) 440, 150.

The foregoing process 510-550 was described in the context of the modular medical device system 110 establishing communication 510 with a medical device(s) 440, 150, and the modular medical device system 110 providing any required updates to the executable code and configuration information to the medical device 440, 150. However, in some implementations the updated executable code and configuration information are provided from a server such as server 410, 415, and/or client 420 to modular medical device system 110. Modular medical device system 110 can then distribute the updates to the medical device(s) 440, 150 according to 510-550.

In some implementations, a complete data package containing a complete set of required executable code and a complete set of required configuration information can be provided from server 410, 415, and/or client 420 to modular medical device system 110, or to medical device 440, 150. The complete data package may be all the data that is needed to operate the medical device 440, 150.

In some implementations, a server such as server 410, 415, and/or client 420 can directly provide any needed executable code updates and/or configuration information updates to a medical device such as medical device 440A or 440D via network 405 or other communication method. For example, medical device 440B or 440C can receive executable code updates or configuration information updates from another medical device such as medical device 440A.

Coordinating executable code updates and configuration information updates in the medical devices assures compatibility of the configuration data and the executable code update stored in the medical device. Moreover, when most or all the processors in the medical device or system are updated together, compatibility between the operating processors can also be assured. Furthermore when all the medical devices in the system are updated together, compatibility between the medical devices in the system can also be assured. By coordinating the configuration information updates and executable code updates, the number of combinations of executable code and configuration information that must be compatible in order for the medical device system to operate correctly is reduced resulting in a more robust and reliable system. Also, by not re-sending updates to executable code or configuration information that medical devices already have, time and bandwidth resources are conserved by eliminating unneeded or duplicate updates.

Figure 6:
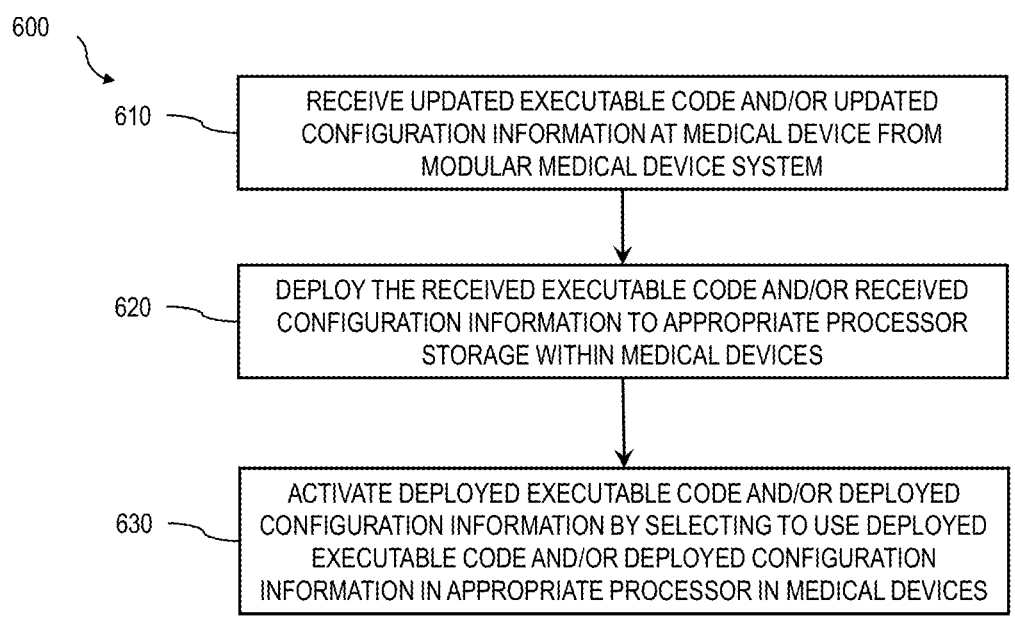
FIG. 6 is an example of a process 600 performed at a medical device to update the executable code and/or configuration information for processors in the medical device.

FIG. 6 is an example of a process 600 performed at a medical device to update executable code (e.g. software) and/or configuration in the medical device. At 610, a medical device receives from a modular medical device system (or server or client) one or more updates to executable code and/or configuration information for the one or more processors in the medical device. At 620, the medical device deploys the received executable code update and/or configuration information update into the memory and/or storage of the appropriate processor in the medical device. At 630, the medical device activates the deployed executable code update and/or configuration information update at a clinically appropriate time. In some implementations, when a medical device contains more than one processor, updating the executable code and/or configuration information associated with each of the more than one processors is followed by rebooting the processors together to ensure compatibility between the processors.

At 610, a medical device 440, 150 receives from a modular medical device system 110 (or server 410, 415, and/or client 420) one or more updates to executable code and/or configuration information for the one or more processors in the medical device 440, 150. For example, a medical device such as medical device 440E may have one processor. In this example, medical device 440E receives an update to the executable code for the processor and also receives an update to the configuration information for the processor. In another example, medical device 440F has five processors. Medical device 440F may receive executable code updates for three of the five processors, and updated configuration information for two processors.

At 620, the medical device 440, 150 deploys the received executable code update and/or configuration information update to the memory or storage of the appropriate processor in the medical device 440, 150. For example, the medical device 440, 150 may store in an interim storage an executable code update for one of the processors in medical device 440, 150 that has been received from the modular medical device system 110. To deploy the received update to executable code means to determine the appropriate processor within the medical device for the received executable code update, and to transfer within the medical device the executable code update to the memory or storage associated with the appropriate processor. To deploy the received configuration information update means to determine the appropriate processor within the medical device for the received configuration information update, and to transfer the received configuration information update to the memory or storage associated with the appropriate processor.

At 630, the medical device 440, 150 activates the deployed executable code update and/or deployed configuration information update at a clinically appropriate time. To activate a deployed update to executable code means to replace or update any existing executable code with the updated code received from the modular medical device system 110 (or from a server or client via the network, or from another medical device), and deployed by the medical device 440, 150. Once activated, the medical device 440, 150 uses the updated executable code and/or configuration information to operate the medical device 440, 150.

Activation can occur at a clinically appropriate time selected by the medical device 440, 150. A clinically appropriate time may be a predetermined time duration after the medical device was turned-off. For example, in some implementations, activation can occur at power-up, when powered-up eight hours after the medical device has been turned off. The time duration required between the when the medical device is turned-off and activation of an update, as well as other conditions required for activation may be part of the updateable configuration information associated with the medical device 440, 150. In some implementations, patient information is logically discarded eight hours after the device is turned-off which is an opportunity to update without interfering with therapy to a patient. In some implementations, the medical device checks at power-up to see how long the device has been off. At power-up, if the medical device has been off for eight hours or more, the medical device may activate the updated executable code and/or configuration information before becoming available to an operator for use. In other implementations, the medical device may wake-up while "turned-off" to perform an activation which assures that when the device is powered-on, the user does not have to wait for the activation to complete (requiring more time than a normal power-up) before becoming available to the operator.

In some implementations, activation is performed when the medical device 440, 150 is powered-up from an off state. In some implementations, activation is performed as the medical device 440, 150 is powered-down. For example, a power switch local to the medical device 440, 150 may provide a power-down command to the medical device 440, 150. When an operator presses the switch to initiate powering down, the medical device can first activate deployed updates before completing a power-down process.

In some implementations, determining a clinically appropriate time to activate an update includes an interaction with the user/operator. For example, an interaction with the user/operator may be needed when activating an update at power-up or power-down. The medical device may be powered-up or powered-down for many reasons including to save power when the medical device is not being used, or to reset medical device settings, and so on. To gather more information to use in determining whether to update now or at a later time, the medical device may display one or more messages to the user/operator. For example, the medical device may display a message such as: "New configuration available—update?" or "New patient?" or "Are you finished with this patient?" The response from the user/operator to these and/or other queries may determine whether an update is performed now or at a later time. The answer(s) to these query(ies) allows the medical device to determine if the power-up or power-down was done during a therapy session with a patient. If performed during a therapy session, the medical device may determine to not update now in order to ensure patient information is not changed or discarded during the therapy session, and to ensure the clinical behavior of the medical device remains the same during the therapy session.

The following U.S. patent application is hereby incorporated by reference in its entirety: U.S. patent application Ser. No. 13/829,744 entitled "Modular Medical Device System", filed Mar. 14, 2013.

One or more aspects or features of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g., mouse, touch screen, etc.), and at least one output device.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

With certain aspects, to provide for interaction with a user, the subject matter described herein can be implemented on a computer having a display device, such as for example a cathode ray tube (CRT) or a liquid crystal display (LCD) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), the Internet, WiFI (IEEE 802.11 standards), NFC, BLUETOOTH, ZIGBEE, and the like.

The computing system may include clients and servers. A client and server are generally remote from each other and typically interact through a communication network. The relationship of client and server arises by virtue of computer programs running on the respective computers and having a client-server relationship to each other.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flow(s) depicted in the accompanying figures and/or described herein do not necessarily require the particular order shown, or sequential order, to achieve desirable results. Other implementations may be within the scope of the following claims.

What is claimed is:

1. A method comprising:
identifying, at a medical device controller that operates in conjunction with a medical device, one or more current versions of executable code associated with one or more processors of a plurality of processors in a medical device;
determining, at the medical device controller, one or more current versions of configuration information associated with the one or more processors in the medical device, the configuration information including patient treatment information;
determining, at the medical device controller, which of the one or more processors among the plurality of processors in the medical device require updated executable code, and which of the one or more processors among the plurality of processors in the medical device require updated configuration information associated with the updated executable code;
distributing, from the medical device controller to the medical device, the updated executable code or the updated configuration information;
determining a clinically appropriate time to activate the updated executable code or the updated configuration information based on the patient treatment information; and
activating the updated executable code or the updated configuration information at the medical device at the clinically appropriate time based on an interaction with a user.

2. The method as in claim 1, wherein the executable code comprises at least one of an operating system and an application.

3. The method as in claim 1, wherein the configuration information comprises values that can be modified by a user, wherein the values affect the functioning of the medical device.

4. The method as in claim 1, wherein at least one communications interface wirelessly couples the medical device controller to the medical device.

5. The method as in claim 1, wherein the medical device comprises a fluid infusion pump.

6. The method as in claim 5, wherein the fluid infusion pump is at least one of: a syringe pump, a patient controlled infusion pump, a large volume infusion pump, and a peristaltic pump.

7. The method as in claim 1, wherein the medical device comprises at least one of: a patient-controlled analgesia (PCA) system, a vital signs monitor, a blood analyte monitor, a cardiac output monitors, a gastric tonometers, an SpO2 sensor, an EtCO2 sensor, an identification module, a barcode scanner, and a radio frequency identification (RFID) scanner.

8. The method as in claim 4, wherein the at least one communications interface is a wired or wireless network connection.

9. The method as in claim 1, wherein the updated configuration information includes a predetermined time duration that must expire before activating the updated executable code.

10. The method as in claim 1, wherein the updated configuration information includes a predetermined time duration that must expire before activating the updated configuration information.

11. A system comprising:
a medical device controller comprising a data processor; and memory storing instructions which, when executed by the data processor, cause operations comprising:
identifying, at a medical device controller that operates in conjunction with a medical device, one or more current versions of executable code associated with one or more processors of a plurality of processors in a medical device;
determining, at the medical device controller, one or more current versions of configuration information associated with the one or more processors in the medical device, the configuration information including patient treatment information;
determining, at the medical device controller, which of the one or more processors among the plurality of processors in the medical device require updated executable code, and which of the one or more processors among the plurality of processors in the medical device require updated configuration information associated with the updated executable code;
distributing, from the medical device controller to the medical device, the updated executable code or the updated configuration information;
determining a clinically appropriate time to activate the updated executable code or the updated configuration information based on the patient treatment information; and
activating the updated executable code or the updated configuration information at the medical device at the clinically appropriate time based on an interaction with a user.

12. The system as in claim 11, wherein the executable code comprises at least one of an operating system and an application.

13. The system as in claim 11, wherein the configuration information comprises values that can be modified by a user, wherein the values affect the functioning of the medical device.

14. The system as in claim 11, wherein the system includes at least one communications interface wirelessly couples the medical device controller to the medical device.

15. The system as in claim 11, further comprising the medical device, and wherein the medical device comprises a fluid infusion pump.

16. The system as in claim 15, wherein the fluid infusion pump is at least one of: a syringe pump, a patient controlled infusion pump, a large volume infusion pump, and a peristaltic pump.

17. The system as in claim 11, further comprising the medical device, and wherein the medical device comprises at least one of: a patient-controlled analgesia (PCA) system, a vital signs monitor, a blood analyte monitor, a cardiac output monitors, a gastric tonometers, an SpO2 sensor, an EtCO2 sensor, an identification module, a barcode scanner, and a radio frequency identification (RFID) scanner.

18. The system as in claim 14, wherein the at least one communications interface is a wired or wireless network connection.

19. The system as in claim 11, wherein the updated configuration information includes a predetermined time duration that must expire before activating the updated executable code.

20. The system as in claim 11, wherein the updated configuration information includes a predetermined time duration that must expire before activating the updated configuration information.

* * * * *